United States Patent [19]
Bennett et al.

[11] Patent Number: 5,543,218
[45] Date of Patent: Aug. 6, 1996

[54] BIOABSORBABLE COPOLYMER AND COATING COMPOSITION CONTAINING SAME

[75] Inventors: Steven L. Bennett, Milford; Mark S. Roby, Madison, both of Conn.

[73] Assignee: United States Surgical Corporation, Norwalk, Conn.

[21] Appl. No.: 440,855

[22] Filed: May 15, 1995

Related U.S. Application Data

[63] Continuation of Ser. No. 75,995, Jun. 11, 1993, abandoned.

[51] Int. Cl.$^6$ .......................... A61B 19/00; D06M 15/00
[52] U.S. Cl. .......................... 428/375; 428/378; 424/422; 424/423
[58] Field of Search .................... 428/375, 378, 428/394, 395; 424/422, 443, 423; 528/354, 355; 523/105

[56] References Cited

U.S. PATENT DOCUMENTS

| | | | |
|---|---|---|---|
| 3,169,945 | 2/1965 | Hostettler et al. | 260/78.3 |
| 3,912,692 | 10/1975 | Casey et al. | 128/333.5 |
| 3,942,532 | 3/1976 | Hunter et al. | 122/333.5 |
| 4,605,730 | 8/1986 | Shalaby et al. | 528/354 |
| 4,624,256 | 11/1986 | Messier et al. | 128/333.5 |
| 4,643,191 | 2/1987 | Bezwada et al. | 128/333.5 |
| 4,700,704 | 10/1987 | Jamiolkowski et al. | 128/333.5 |
| 4,788,979 | 12/1988 | Jarrett et al. | 528/354 |
| 4,791,929 | 12/1988 | Jarrett et al. | 528/354 |
| 4,994,074 | 2/1991 | Bezwada et al. | 606/230 |
| 5,076,807 | 12/1991 | Bezwada et al. | 606/230 |
| 5,080,665 | 1/1992 | Jarrett et al. | 606/230 |
| 5,085,629 | 2/1992 | Goldberg et al. | 604/8 |
| 5,100,433 | 3/1992 | Bezwada et al. | 606/230 |
| 5,116,932 | 5/1992 | Fujiwa | 528/80 |
| 5,210,108 | 5/1993 | Spinu et al. | 521/182 |
| 5,225,521 | 7/1993 | Spinu | 528/354 |
| 5,278,202 | 1/1994 | Dunn et al. | 523/113 |
| 5,352,515 | 10/1994 | Jarrett et al. | 428/357 |
| 5,399,666 | 3/1995 | Ford | 528/354 |

FOREIGN PATENT DOCUMENTS

| | | |
|---|---|---|
| 0117538 | 9/1984 | European Pat. Off. . |
| WO84/04311 | 11/1984 | WIPO . |

OTHER PUBLICATIONS

Grijpma et al., "Star-shaped polylactide-containing block copolymers", Makromol. Chem., Rapid Commun. vol. 14, pp. 155–161 (1993).

Primary Examiner—Stevan A. Resan

[57] ABSTRACT

A bioabsorbable copolymer is obtained from the polymerization of a major amount of ε-caprolactone and a minor amount of at least one other copolymerizable monomer in the presence of a polyhydric alcohol initiator. The copolymer is useful, inter alia, as a coating for a surgical suture.

12 Claims, No Drawings

BIOABSORBABLE COPOLYMER AND COATING COMPOSITION CONTAINING SAME

This is a continuation of application Ser. No. 08/075.995, filed on Jun. 11, 1993, now abandoned.

BACKGROUND OF THE INVENTION

This invention relates to a bioabsorbable copolymer and, more particularly, to a bioabsorbable copolymer obtained by polymerizing a major amount of $\epsilon$-caprolactone and a minor amount of at least one other copolymerizable monomer in the presence of a polyhydric alcohol initiator.

U.S. Pat. No. 3,169,945 discloses a homopolymer of $\epsilon$-caprolactone obtained by polymerizing $\epsilon$-caprolactone in the presence of a polyhydric alcohol initiator such as glycerol, erythritol, sorbitol, etc.

U.S. Pat. No. 3,912,692 discloses a homopolymer of glycolide and a copolymer derived from glycolide and lactide obtained by polymerizing the monomers in the presence of inositol as initiator.

U.S. Pat. No. 3,942,532 discloses a suture coating composition obtained by polymerizing lactones such as $\epsilon$-caprolactone in the presence of a polymethylenediol.

Copolymers derived from $\epsilon$-caprolactone and at least one other monomer such as glycolide, lactide, p-dioxanone and trimethylene carbonate are disclosed in U.S. Pat. Nos. 4,605,730, 4,624,256, 4,700,704, 4,788,979, 4,791,929, 4,994,074, 5,076,807, 5,080,665, 5,085,629 and 5,100,433.

U.S. Pat. No. 4,624,256 discloses, inter alia, a copolymer derived from a major amount of $\epsilon$-caprolactone and a minor amount of a linear aliphatic diol such as butanediol and hexanediol.

U.S. Pat. No. 4,643,191 discloses a copolymer derived from the polymerization of p-dioxanone in the presence of an initiator, e.g., an alkanol or a glycol, to form a mixture of p-dioxanone homopolymer and unreacted monomer with subsequent polymerization of the mixture with lactide to form the copolymer.

U.S. Pat. No. 5,076,807 discloses a copolymer prepared by polymerizing p-dioxanone with glycolide and/or lactide in the presence of an initiator such as a polyhydric alcohol, e.g., glycerol, mannitol, etc.

SUMMARY OF THE INVENTION

In accordance with the present invention, a bioabsorbable copolymer is obtained by polymerizing a major amount of $\epsilon$-caprolactone and a minor amount of at least one other copolymerizable monomer in the presence of a polyhydric alcohol initiator.

The use of a polyhydric alcohol initiator, i.e., an alcohol possessing three or more hydroxyl groups, provides a copolymer having a branched, or "star", configuration. The branched structure of the bioabsorbable copolymer herein exerts a characteristic influence on its bioabsorption behavior making it useful, among other applications, as a surgical suture coating material.

DESCRIPTION OF THE PREFERRED EMBODIMENTS

Conventional polymerization techniques that are well known and disclosed in the prior art can be utilized in preparing the bioabsorbable copolymer of the present invention. The bioabsorbable copolymer is obtained by polymerizing a major amount of $\epsilon$-caprolactone and a minor amount of at least one other copolymerizable monomer or mixture of such monomers in the presence of a polyhydric alcohol initiator. The polymerization of these monomers contemplates all of the various types of monomer addition, i.e., simultaneous, sequential, simultaneous followed by sequential, sequential followed by simultaneous, etc.

Suitable monomers which can be copolymerized with $\epsilon$-caprolactone include glycolide, lactide, p-dioxanone and trimethylene carbonate.

Suitable polyhydric alcohol initiators include glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N', N'-tetrakis(2-hydroxyethyl)ethylenediamine, N,N,N', N'-tetrakis(2-hydroxypropyl)ethylenediamine, dipentaerythritol, allitol, dulcitol, glucitol, altritol, iditol, sorbitol, mannitol, inositol, and the like.

The copolymer herein can contain from about 70 to about 98, and preferably from about 80 to about 95, weight percent $\epsilon$-caprolactone-derived units, the balance of the copolymer being derived from the other copolymerizable monomer(s). The inherent viscosity of the copolymer generally ranges from about 0.10 to about 0.60, and preferably from about 0.20 to about 0.50, dl/g when measured in chloroform at a concentration of 0.2500 g/dl at 30° C. The polyhydric alcohol initiator is generally employed in small amounts, e.g., from about 0.5 to about 5, and preferably from about 0.1 to about 2, weight percent of the total monomer mixture.

The bioabsorbable copolymer of the present invention is non-toxic and physiologically inert. Depending on its particular physical and bioabsorption properties (to a large extent influenced by the nature of the initiator and monomers from which it is prepared), the bioabsorbable copolymer herein can be used in the fabrication in whole or in part of a variety of implantable medical devices and prostheses, e.g., clips, staples, sutures, suture coatings, etc. Applied to a suture, a coating composition containing the bioabsorbable copolymer of the invention results in a significant improvement in one or more properties of the suture, e.g., its lubricity, knot tiedown and/or knot security characteristics.

The bioabsorbable copolymer herein can be applied to a suture by any suitable process, e.g., passing the suture through a solution of the copolymer, e.g., in acetone, methylene chloride, etc., past a brush or other coating solution applicator, or past one or more spray nozzles dispensing the suture coating solution. The suture wetted with the coating solution is subsequently passed through or held in a drying oven for a time and at a temperature sufficient to vaporize and drive off the solvent. If desired, the suture coating composition can optionally contain additional components, e.g., dyes, antibiotics, antiseptics, growth factors, anti-inflammatory agents, etc.

While the coating composition herein can be applied to any type of suture, it is essentially intended for application to a braided suture, a preferred type of which is disclosed in U.S. Pat. No. 5,019,093, the contents of which are incorporated by reference herein. The amount of coating composition applied to a braided suture will vary depending upon the structure of the suture, e.g., the number of filaments, tightness of braid or twist, the size of the suture and its composition.

The coating composition herein can be used for both "unfilled" as well as "filled" sutures, the latter designating braided bioabsorbable sutures containing a storage stabilizing material as disclosed in U.S. Pat. Nos. 5,037,429 or 5,051,272, the contents of which are incorporated by reference herein. For an "unfilled" suture, the coating composition can be applied at a level of from about 0.5 to about 4 weight percent or more and preferably from about 1 to about 3 weight percent. Advantageously, the coating composition is applied to the suture prior to application of the storage stabilizing material. For a filled suture, the amount of applied coating composition can range from about 0.2 to as much as about 3 weight percent or more and preferably from about 0.5 to about 2 weight percent. As a practical matter, it is generally preferred to apply the minimum amount of coating composition consistent with good tie-down performance. This level of coating add-on can be readily determined for any particular suture coating system employing routine experimental procedures.

In the case of an unfilled or filled braided suture, prior to application of the coating composition, it can be advantageous to calender the suture in order to improve the uniformity with which the coating composition is laid down upon the suture surface. A calendering operation can also be beneficial when carried out on a coated suture where the suture is to be filled with a storage stabilizing material. In this case, calendering will tend to break up the coating facilitating penetration of the interior spaces of the suture by the storage stabilizing material.

A preferred method for calendering a braided suture and an apparatus for carrying out the method are disclosed in copending U.S. patent application Ser. No. 07/652,939, filed Feb. 8, 1991, the contents of which are incorporated by reference herein. In accordance with Serial No. 07/652,939, calendering of a braided suture is achieved by applying a compressive force to the suture in a first line or direction generally transverse to the longitudinal direction of the suture, the compressive force being of sufficient magnitude as to flatten the suture in a direction orthogonal to the direction in which the compressive force is applied. Preferably, a second application of compressive force is applied to the suture in a direction generally transverse to that of the first compressive force and transverse to the longitudinal direction of the suture. The second compressive force is substantially equal in magnitude to the first compressive force so that the suture returns to its original cross-sectional configuration.

The apparatus for implementing the foregoing calendering method includes at least one pair of rollers which are biased towards each other to apply a compressive force to the suture as the suture passes between them. Optionally, a second pair of rollers is provided which is oriented at an angle (preferably 90°) to the first pair of rollers and transverse to the longitudinal direction of the suture. Following passage between both the first and second pair of rollers, the suture will have been alternately compressed, or flattened, in a first direction and thereafter in a second direction at an angle to the first direction.

The following examples are illustrative of the bioabsorbable copolymer of this invention, its preparation and its application as a coating to sutures.

EXAMPLES 1–11

Dry glycolide (300.0 g), $\epsilon$-caprolactone (2760 g), stannous octoate as catalyst (0.3 g) and dry mannitol as initiator (39.0 g) were mixed under $N_2$ for one hour. The mixture was heated in a reactor at a temperature of 160° C. for 24 hours. Greater than 95 percent conversion of monomers to copolymer was obtained. The resultant copolymer was dissolved in methylene chloride and braided surgical sutures were drawn through the solution to coat the sutures with the coating composition (Examples 1–11). After drying the sutures in an oven for 96 hours, performance characteristics of the sutures, e.g., Surgeon's Throw, Knot Reposition and Knot Security, were measured on a standard tie board.

A tie board consists of a base on which two plates are perpendicularly affixed. These plates are parallel to one another on the base and are separated by a distance of at least 3 inches. Each plate contains two oppositely disposed openings, the distance between the openings on one plate being longer than that of the other plate. An elastic tube is passed through the openings on both plates to complete a loop which is then tied to secure the loop to the plates. The loop is in the general configuration of an isosceles triangle. To perform the Surgeon's Throw and Knot Reposition tests as described below, a suture is looped and tied around the elastic tube of the tie board and tied. The elastic tube exerts an outward force on the suture knot. This force approximates the force exerted by living tissue on suture knots. Thus, the tie board is an effective means of evaluating the performance characteristics of surgical sutures.

The procedures for evaluating these performance characteristics are described in Table I as follows:

TABLE I

PROCEDURES FOR MEASURING PERFORMANCE CHARACTERISTICS OF SUTURES COATED WITH $\epsilon$-CAPROLACTONE-GLYCOLIDE COPOLYMERS

| Performance Characteristic | Test Procedure |
| --- | --- |
| Surgeon's Throw | A suture is looped around the elastic tubes of a tie board and tied with a surgeon's throw (a half hitch with an extra loop of the free end). The ends are pulled apart by hand and the suture loop pulls the elastic tubes of the tie board together. The ends of the suture are then released. If the tubes stay together for approximately ten seconds, the trial is counted as a "pass". If the surgeon's throw slips and the tubes move apart, the trial is counted as a "failure". |
| Knot Reposition | A suture is looped around the elastic tubes of a tie board and tied with two half hitches in the same direction (a granny knot). The free ends of the suture are pulled apart by hand. If the knot slips and the loop of the suture pulls the elastic tubes of the tie board together, the knot is said to reposition and the trial is counted as a "pass". If the suture breaks or if the knot locks in place and cannot be moved, the trial is counted as a "failure". |
| Knot Security | A 2 cm loop is tied with a |

TABLE I-continued

PROCEDURES FOR MEASURING PERFORMANCE
CHARACTERISTICS OF SUTURES COATED WITH
ε-CAPROLACTONE-GLYCOLIDE COPOLYMERS

| Performance Characteristic | Test Procedure |
|---|---|
| | surgeon's square knot (1 = 1 = 1 = 1) securing the throws at 20% of the USP XXII knot strength for 2/0 nonabsorbable sutures (n = 10 loops per group). The loop is placed next to a cloth-wrapped mandrel rotating at .5 rpm. The fixtures are secured to allow contact of the cloth material against the fourth throw or, top throw, of each knot. The cloth wrapping is moistened with 37° C. water prior to the test and is periodically remoistened during the test. For each pass of the cloth across the knot (for a total of 100 passes), the knot is inspected for top throw security. For a knot to be considered secure, there must be no relaxation of the knot or loss of the fourth throw. |

Test results are set forth in Table II below:

TABLE II

PERFORMANCE CHARACTERISTICS OF SUTURES
COATED WITH MANNITOL-INITIATED 90:10
CAPROLACTONE:GLYCOLIDE COPOLYMER

| Example | Coating Level (%) | Surgeon's Throw (No. of passes/ 10 attempts) | Knot Reposition (No. of passes/ 10 attempts) | Knot Security (No. of throws to secure) |
|---|---|---|---|---|
| 1 | 0.8 | 2 | 10 | 3 |
| 2 | 1.3 | 2 | 10 | 3 |
| 3 | 1.6 | 4 | 10 | 3 |
| 4 | 1.7 | 0 | 9 | 4 |
| 5 | 1.9 | 2 | 10 | 6 |
| 6 | 0.7 | 5 | 10 | 3 |
| 7 | 1.2 | 1 | 10 | 3 |
| 8 | 1.8 | 7 | 10 | 4 |
| 9 | 0.8 | 7 | 10 | 4 |
| 10 | 1.3 | 7 | 10 | 5 |
| 11 | 1.6 | 7 | 10 | 3 |

The above data show that the knot repositioning characteristics of sutures coated with the mannitol-initiated copolymers of Examples 1–11 are excellent. Specifically, 10 successful passes out of 10 attempts were obtained for 10 of the 11 examples.

EXAMPLES 12–16 AND COMPARATIVE EXAMPLES 1–7

Performance characteristics, i.e, Surgeon's Throw and Knot Reposition, were evaluated for the following braided sutures:

(1) sutures coated with a 90:10 weight percent mannitol-initiated caprolactone-glycolide branched, i.e., "star", copolymer (Examples 12–16);

(2) sutures coated with a 90:10 weight percent diethylene glycol-initiated caprolactone-glycolide linear copolymer (Comparative Examples 1–5);

(3) sutures coated with a block copolymer comprising 35 weight percent polypropylene glycol as one block and 65 weight percent of an 18:82 weight percent glycolide:lactide copolymer as the other block (Comparative Example 6); and, (4) uncoated braided sutures (Comparative Example 7: Vicryl® brand of Ethicon, Inc.).

The results of the Surgeon's Throw and Knot Reposition tests are set forth in Table III as follows:

TABLE III

PERFORMANCE CHARACTERISTICS
OF COATED SUTURES

| | Coating Level (%) | Surgeon's Throw (No. of passes/ 10 attempts) | Knot Reposition (No. of passes/ 10 attempts) |
|---|---|---|---|
| Example | | | |
| 12 | 0.46 | 8 | 10 |
| 13 | 0.60 | 10 | 10 |
| 14 | 0.94 | 7 | 10 |
| 15 | 1.10 | 9 | 9 |
| 16 | 1.30 | 9 | 10 |
| Comparative Example | | | |
| 1 | 0.79 | 10 | 9 |
| 2 | 0.92 | 9 | 6 |
| 3 | 0.97 | 10 | 10 |
| 4 | 1.10 | 10 | 10 |
| 5 | 1.20 | 10 | 8 |
| 6 | — | 10 | 6 |
| 7 | — | 10 | 7 |

In addition to the performance characteristics of Examples 12–16 and Comparative Examples 1–7 reported in Table III above, several of the braided sutures were further evaluated for Force Required for Run Down.

Force Required for Run Down was performed using a tie board designed to be attached to an Instron 4301 and to match the properties of a standard tie board. This tie board consists of two parallel tubes which were adjusted so that the same force was required to close both the standard tie board and the Instron tie board. On both sides of the tubing and at the same level as the tubing, wheels were mounted so that the forces exerted on the free ends of the knot were at 180°. The bottom grip of the Instron was removed and the tie board was mounted in its place. The same knot as is tied for Knot Repositioning was tied around the tubing of the Instron tie board. The free ends were looped under the two wheels and up to the top grip on the Instron. The Instron cross-head moved upward at 500 mm per minute, thus running the knot down until the tubes were closed and the knot broke. A plot of the load versus the displacement was created and from this plot the force at the first inflection was recorded as the force required to run the knot down.

Ten samples were tested, the average measured value being set forth in Table IV below:

TABLE IV

PERFORMANCE CHARACTERISTICS
OF COATED SUTURES

| Example | Mean Force Required for Run Down* |
|---|---|
| 14 | 2.47 |
| Comparative Example | |
| 3 | 3.35 |
| 6 | 4.42 |
| 7 | 2.81 |

*In each example, 10 suture samples were tested except for Comparative Example 3 for which 9 suture samples were tested.

The above results clearly demonstrate that the suture coated with the copolymer of this invention (Example 14) required the least amount of force to reposition a knot relative to the Comparative Examples. Therefore, these data show that coating sutures with a star copolymer leads to significantly improved handling characteristics in sutures relative to suture coatings derived from a linear copolymer possessing an identical composition.

What is claimed is:

1. A surgical suture coated with a coating composition comprising a branched or star shaped bioabsorbable copolymer obtained by polymerizing a major amount of ε-caprolactone and a minor amount of at least one other copolymerizable monomer in the presence of polyhydric alcohol having 3 or more hydroxy groups as initiator, said suture exhibiting a mean force for achieving knot run down which is less than that exhibited by a suture coated with a coating composition which is obtained in the same manner but with a dihydric alcohol as initiator.

2. The surgical suture of claim 1 which is a bioabsorbable braided suture.

3. The suture of claim 1 wherein the other copolymerizable monomer is selected from the group consisting of glycolide, lactide, p-dioxanone and trimethylene carbonate.

4. The suture of claim 1 wherein the polyhydric alcohol initiator is selected from the group consisting of glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N, N', N'-tetrakis(2-hydroxyethyl)ethylenediamine, N,N,N',N'-tetrakis(2-hydroxypropyl)ethylenediamine, dipentaerythritol, allitol, dulcitol, glucitol, altritol, iditol, sorbitol, mannitol and inositol.

5. The suture of claim 1 wherein the copolymer contains from about 70 to about 98 weight percent ε-caprolactone-derived units, the balance of the copolymer being derived from the other copolymerizable monomer(s).

6. The suture of claim 1 wherein the copolymer contains from about 80 to about 95 weight percent ε-caprolactone-derived units, the balance of the copolymer being derived from the other copolymerizable monomer(s).

7. The suture of claim 1 wherein the copolymer possesses an inherent viscosity from about 0.10 to about 0.60 dl/g when measured in chloroform at a concentration of 0.2500 g/dl at 30° C.

8. The suture of claim 1 wherein the copolymer possesses an inherent viscosity from about 0.20 to about 0.50 dl/g when measured in chloroform at a concentration of 0.2500 g/dl at 30° C.

9. The suture of claim 1 wherein the polyhydric alcohol initiator is employed in an amount of from about 0.5 to about 5 weight percent of the total monomer mixture.

10. The suture of claim 1 wherein the polyhydric alcohol initiator is employed in an amount of from about 0.1 to about 2 weight percent of the total monomer mixture.

11. The suture of claim 1 wherein the coating composition is applied to a suture at a level of from about 0.2 to about 4 weight percent of the entire coated suture.

12. The suture of claim 1 wherein the coating composition is applied to a suture at a level of from about 0.5 to about 3 weight percent of the entire coated suture.

* * * * *